US00PP25619P2

(12) United States Plant Patent
Schaber

(10) Patent No.: US PP25,619 P2
(45) Date of Patent: Jun. 16, 2015

(54) GERANIUM PLANT NAMED 'OGLGER8026'

(50) Latin Name: *Pelargonium×domesticum*
Varietal Denomination: Oglger8026

(71) Applicant: Margaret Schaber, Encinitas, CA (US)

(72) Inventor: Margaret Schaber, Encinitas, CA (US)

(73) Assignee: Dümmen Group B.V., De Lier (NL)

( * ) Notice: Subject to any disclaimer, the term of this patent is extended or adjusted under 35 U.S.C. 154(b) by 148 days.

(21) Appl. No.: 13/986,836

(22) Filed: Jun. 10, 2013

(51) Int. Cl.
*A01H 5/00* (2006.01)

(52) U.S. Cl.
USPC ..... Plt./331

(58) Field of Classification Search
USPC ..... Plt./331
See application file for complete search history.

*Primary Examiner* — Anne Grunberg
(74) *Attorney, Agent, or Firm* — C. A. Whealy

(57) ABSTRACT

A new and distinct cultivar of Regal Geranium plant named 'Oglger8026', characterized by its upright and mounded plant habit; moderately vigorous growth habit; relatively small leaves; freely flowering habit with flowers held above the foliar plane; and large dark burgundy-colored flowers with red purple-colored picotee-type margins, and white-colored throats.

1 Drawing Sheet

Botanical designation: *Pelargonium×domesticum.*
Cultivar denomination: 'OGLGER8026'.

BACKGROUND OF THE INVENTION

The present invention relates to a new and distinct cultivar of Regal Geranium plant, botanically known as *Pelargonium×domesticum*, and hereinafter referred to by the name 'Oglger8026'.

The new Regal Geranium plant is a product of a planned breeding program conducted by the Inventor in Lompoc, Calif. The objective of the breeding program is to create new Regal Geranium plants with numerous attractive flowers.

The new Regal Geranium plant originated from a cross-pollination made by the Inventor in December, 2006 in Lompoc, Calif. of a proprietary selection of *Pelargonium×domesticum* identified as code number 169, not patented, as the female, or seed, parent with a proprietary selection of *Pelargonium×domesticum* identified as code number 151, not patented, as the male, or pollen, parent. The new Regal Geranium plant was discovered and selected by the Inventor as a single flowering plant from within the progeny of the stated cross-pollination in a controlled greenhouse environment in Lompoc, Calif. in April, 2008.

Asexual reproduction of the new Regal Geranium plant by vegetative cuttings in a controlled greenhouse environment in Connellsville, Pa. since September, 2008 has shown that the unique features of this new Regal Geranium plant are stable and reproduced true to type in successive generations.

SUMMARY OF THE INVENTION

Plants of the new Regal Geranium have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Oglger8026'.

These characteristics in combination distinguish 'Oglger8026' as a new and distinct Regal Geranium plant:

1. Upright and mounded plant habit.
2. Moderately vigorous growth habit.
3. Relatively small leaves.
4. Freely flowering habit with flowers held above the foliar plane.
5. Large dark burgundy-colored flowers with red purple-colored picotee-type margins, and white-colored throats.

Plants of the new Regal Geranium differ primarily from plants of the female parent selection in flower color as plants of the female selection have duller burgundy-colored flowers. In addition, plants of the new Regal Geranium have smaller leaves than plants of the female parent selection.

Plants of the new Regal Geranium differ primarily from plants of the male parent selection in flower color as plants of the male selection have pink and rose-colored flowers. In addition, plants of the new Regal Geranium have smaller leaves than plants of the male parent selection.

Plants of the new Regal Geranium can be compared to plants of *Pelargonium×domesticum* 'Pacahal', disclosed in U.S. Plant Pat. No. 16,757. In side-by-side comparisons conducted in Encinitas, Calif., plants of the new Regal Geranium differed primarily from plants of 'Pacahal' in the following characteristics:

1. Plants of the new Regal Geranium were more upright than plants of 'Pacahal'.
2. Plants of the new Regal Geranium and 'Pacahal' differed in flower color as plants of 'Pacahal' had red purple and pink bi-colored flowers.

BRIEF DESCRIPTION OF THE PHOTOGRAPHS

The accompanying colored photographs illustrate the overall appearance of the new Regal Geranium plant showing the colors as true as it is reasonably possible to obtain in colored reproductions of this type. Colors in the photographs may differ slightly from the color values cited in the detailed botanical description which accurately describe the colors of the new Regal Geranium plant.

The photograph at the bottom of the sheet comprises a side perspective view of a typical flowering plant of 'Oglger8026' grown in a container.

The photograph at the top of the sheet is a close-up view of a typical flowering plant of 'Oglger8026'.

DETAILED BOTANICAL DESCRIPTION

The aforementioned photographs and following observations, measurements and values describe plants grown during the winter in 12.7-cm containers in a glass-covered greenhouse in Connellsville, Pa. and under cultural practices typical of Regal Geranium commercial production. During the production of the plants, day temperatures averaged 18° C. and night temperatures averaged 14° C. Plants were eleven weeks old when the photographs and the description were taken. In the detailed description, color references are made to The Royal Horticultural Society Colour Chart, 2007 Edition, except where general terms of ordinary dictionary significance are used.

Botanical classification: *Pelargonium×domesticum* 'Oglger8026'.

Parentage:

*Female, or seed, parent*.—Proprietary selection of *Pelargonium×domesticum* identified as code number 169, not patented.

*Male or pollen parent*.—Proprietary selection of *Pelargonium×domesticum* identified as code number 151, not patented.

Propagation:

*Type*.—By vegetative cuttings.

*Time to initiate roots, summer*.—About ten days at temperatures of 20° C.

*Time to initiate roots, winter*.—About two weeks at temperatures of 16° C.

*Time to produce a rooted young plant, summer*.—About four weeks at temperatures of 20° C.

*Time to produce a rooted young plant, winter*.—About four weeks at soil temperatures of 16° C.

*Root description*.—Medium in thickness, fleshy; white in color.

*Rooting habit*.—Moderate branching; medium density.

Plant description:

*Plant and growth habit*.—Upright and mounding plant habit; moderately vigorous growth habit.

*Branching habit*.—Freely branching habit with about six primary lateral branches developing per plant, each primary lateral branch with two to three secondary lateral branches; dense and bushy appearance; pinching enhances lateral branch development.

*Plant height, to top of umbels*.—About 19 cm.

*Plant height, to top of foliar plane*.—About 15 cm.

*Plant diameter* (*spread*).—About 24.5 cm.

*Lateral branches*.—Length: About 6.2 cm. Diameter: About 5 mm. Internode length: About 1.1 cm. Texture: Pubescent; minute. Strength: Strong. Color: Close to 146A.

Leaf description:

*Arrangement*.—Alternate; simple.

*Length*.—About 5 cm.

*Width*.—About 6.6 cm.

*Shape*.—Semi-circular; palmately lobed.

*Apex*.—Acute.

*Base*.—Roughly truncate.

*Margin*.—Serrate and deeply lobed.

*Venation pattern*.—Palmate, reticulate.

*Texture, upper and lower surfaces*.—Pubescent; leathery.

*Color*.—Developing leaves, upper and lower surfaces: Close to 137C. Fully expanded leaves, upper surface: Close to 137A; venation, close to N138B; no discernable zonation pattern. Fully expanded leaves, lower surface: Close to 147B; venation, close to 148C.

*Petiole*.—Length: About 6.8 cm. Diameter: About 3 mm. Texture, upper and lower surfaces: Pubescent. Color, upper surface: Close to 146A. Color, lower surface: Close to 146B.

Flower description:

*Flower arrangement*.—Nearly round flowers arranged in hemispherical umbels arising from apical leaf axils; umbels displayed above and beyond the foliar plane on strong peduncles; umbels upright and flowers face upright or outwardly.

*Fragrance*.—None detected.

*Quantity of flowers*.—Freely flowering habit; about five open flowers and one to two flower buds per umbel and about six umbels per plant at one time.

*Flowering season*.—In California, flowering is continuous during the spring; plants begin flowering about ten weeks after planting.

*Flower longevity*.—Individual flowers last about three to four days on the plant; flowers not persistent.

*Umbel height*.—About 6.2 cm.

*Umbel diameter*.—About 9.2 cm.

*Flower diameter*.—About 6.6 cm.

*Flower depth* (*height*).—About 2.8 cm to 3.3 cm.

*Flower buds*.—Length: About 2.1 cm. Diameter: About 1 cm. Shape: Elongated oval. Color: Close to N186B.

*Petals*.—Quantity per flower and arrangement: Typically six in a single whorl. Length: About 4.6 cm. Width: About 3.7 cm. Shape: Fan-shaped. Apex: Rounded. Base: Attenuate. Margin: Entire; slightly undulate proximally. Texture, upper and lower surfaces: Smooth, glabrous; satiny to velvety. Color: When opening, upper surface: Close to N186C; picotee-type margin, close to 67C. When opening, lower surface: Ground color, close to 67A; central blotch, close to 187B. Fully opened, upper surface: Close to N92A; picotee-type margin, close to 67B to 67C; base, close to NN155D; venation, close to 187A; color does not fade with development. Fully opened, lower surface: Close to 187A to 187B; color does not fade with development.

*Sepals*.—Quantity per flower: Typically five or six arranged in a single whorl. Length: About 2. cm. Width: About 6 mm. Shape: Lanceolate. Apex: Acuminate; reflexed. Base: Truncate. Margin: Entire. Texture, upper and lower surfaces: Pilose. Color, upper surface: Close to 146B. Color, lower surface: Close to 146A.

*Peduncle* (*umbel stem*).—Length: About 6.3 cm. Diameter: About 2.5 mm. Angle: About 45° from stem axis. Strength: Strong. Texture: Pubescent. Color: Close to 137B.

*Pedicel* (*individual flower stem*).—Length: About 1.8 cm. Diameter: About 1.5 mm. Angle: About 15° from peduncle axis. Strength: Strong. Texture: Pilose. Color: Close to 146B.

*Reproductive organs*.—Androecium: Stamen quantity per flower: About six to nine. Filament length: About 1.3 cm. Filament color: Close to NN155D. Anther length: About 3 mm. Anther shape: Oblong. Anther color: Close to 71A. Pollen amount: Moderate. Pollen color: Close to 175B. Gynoecium: Pistil quantity per flower: One. Pistil length: About 2.2 cm. Stigma shape: Six-parted, star-shaped. Stigma color: Close to 187B. Style length: About 1.2 cm. Style color: Close to 71C. Ovary color: Close to 148D.

*Seeds and fruits*.—Seed and fruit development have not been observed on plants of the new Regal Geranium.

Disease & pest resistance: Plants of the new Regal Geranium have not been observed to be resistant to pathogens and pests common to Regal Geranium plants.

Temperature tolerance: Plants of the new Regal Geranium have been observed to tolerate temperatures ranging from about 1° C. to about 35° C.

It is claimed:

1. A new and distinct Regal Geranium plant named 'Oglger8026' as illustrated and described.

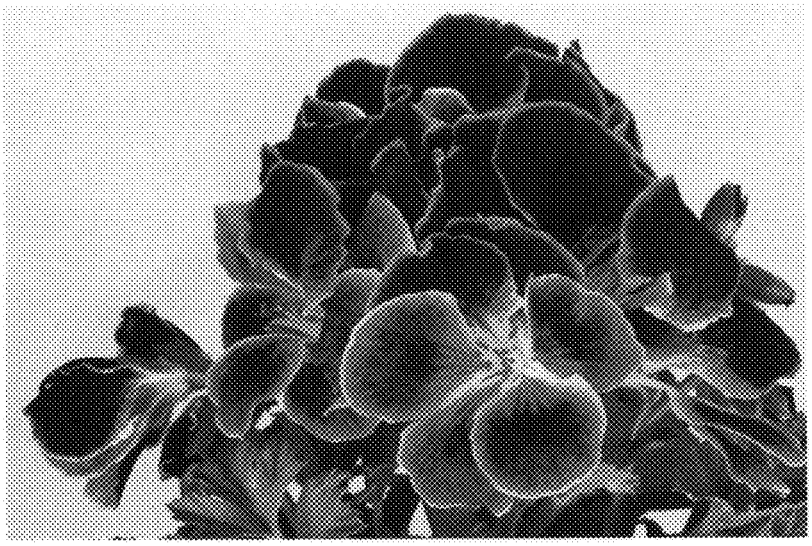
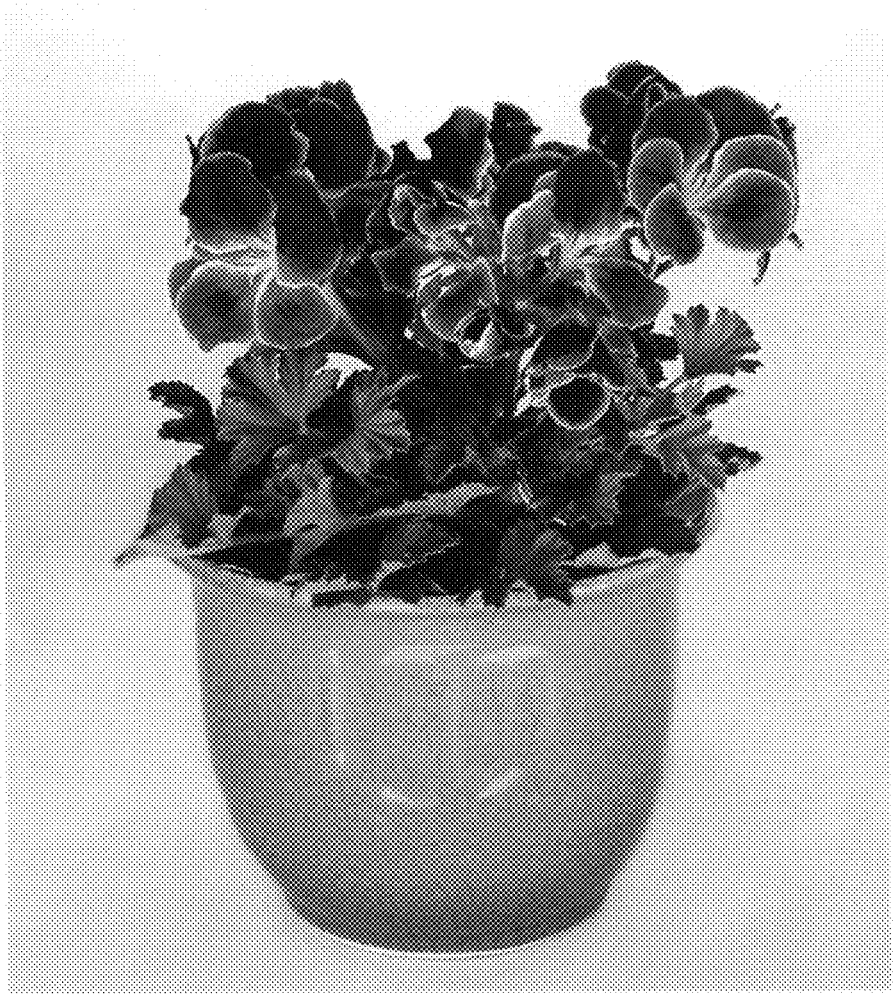

* * * * *